(12) United States Patent
Wofford et al.

(10) Patent No.: US 6,260,999 B1
(45) Date of Patent: Jul. 17, 2001

(54) ISOCENTER LOCALIZATION USING ELECTRONIC PORTAL IMAGING

(75) Inventors: Mark Wofford, Martinez; Francisco M. Hernandez-Guerra, Concord, both of CA (US)

(73) Assignee: Siemens Medical Systems, Inc., Iselin, NJ (US)

(*) Notice: Subject to any disclaimer, the term of this patent is extended or adjusted under 35 U.S.C. 154(b) by 0 days.

(21) Appl. No.: 09/360,927

(22) Filed: Jul. 26, 1999

(51) Int. Cl.[7] .................................................. A61B 18/00
(52) U.S. Cl. .......................... 378/205; 378/204; 378/163; 378/164
(58) Field of Search .................................. 378/204, 205, 378/162, 163, 164

(56) References Cited

U.S. PATENT DOCUMENTS

| | | | |
|---|---|---|---|
| 4,123,660 | 10/1978 | Horwitz | 378/65 |
| 4,223,227 | 9/1980 | Horwitz | 378/206 |
| 4,578,806 | * 3/1986 | Grass et al. | 378/162 |
| 4,722,336 | * 2/1988 | Kim et al. | 606/130 |
| 4,922,512 | 5/1990 | Lajus et al. | 378/197 |
| 5,129,911 | * 7/1992 | Siczek et al. | 600/429 |
| 5,138,647 | 8/1992 | Nguyen et al. | 378/189 |
| 5,263,074 | * 11/1993 | Sakamoto | 378/99 |
| 5,299,254 | * 3/1994 | Dancer et al. | 378/163 |
| 5,446,548 | 8/1995 | Gerig et al. | 356/375 |
| 5,467,193 | 11/1995 | Laewen et al. | 356/399 |
| 5,792,146 | * 8/1998 | Cosman | 606/130 |
| 5,835,563 | * 11/1998 | Navab et al. | 378/207 |
| 6,044,132 | * 3/2000 | Navab | 378/163 |
| 6,118,845 | * 9/2000 | Simon et al. | 378/62 |

* cited by examiner

*Primary Examiner*—Robert H. Kim
*Assistant Examiner*—Allen C. Ho

(57) ABSTRACT

According to an embodiment of the present invention, an isocenter of an image may be found by using a multi-leaf collimator. According to this embodiment, a center leaf is projected into the center of the x-ray field with all other leaves retracted. An image is acquired. A line through the center of the center leaf is identified. This line is also a line through isocenter. Another method according to an embodiment of the present invention for finding isocenter uses an accessory. The accessory according to an embodiment of the present invention includes a metal marker in the center of the accessory with metal markers interspersed away from the center at a predetermined interval. An image may be acquired through the accessory, with the patient on the table. The resulting image may be analyzed to identify the position of the metal markers to determine isocenter.

25 Claims, 8 Drawing Sheets

ISOCENTER LOCALIZATION USING ELECTRONIC PORTAL IMAGING

FIELD OF THE INVENTION

The present invention relates to imaging systems, typically used for radiation treatment. In particular, the present invention relates to imaging systems for linear accelerators (linacs) which may be used in radiation therapy.

BACKGROUND OF THE INVENTION

The use of a linear accelerator in radiation therapy is generally known. Such linear accelerators are typically used for treating patients with x-rays or electron beams. Such x-rays are created when high energy electrons are decelerated in a target material such as tungsten. Alternatively, the electrons themselves may be used directly for treatment.

The major modules in a linear accelerator typically include a movable gantry with a treatment head, a stand, a control console and a treatment couch. The stand is typically anchored firmly to the floor and the gantry typically rotates on bearings in the stand. The operational accelerator structure, housed in the gantry, typically rotates about a horizontal axis fixed by the stand for treatment of a patient lying on the treatment couch.

In the radiation therapy treatment of a patient, geometric accuracy is a very important factor to the success of the treatment. The goal is commonly to hit a specific target, such as a tumor, and miss critical regions of the patient's body, such as the spine. Properly positioning the patient may be a critical issue in avoiding damage to tissue and critical organs. Typically, within reason, the more accurate the x-ray delivery to the exact target, the higher the dose a patient may receive.

An electronic portal image may be captured for the purpose of determining whether the target on the patient is within the treatment beam and whether critical regions of the patient are missed. Typically, people are responsible for taking these images and determining if the patient is positioned correctly. If film is used for the image, then the film must typically be developed and placed next to a reference image to compare the two images. The reference image is typically an x-ray image, which has been marked up by the patient's doctor. The two images are typically compared to ensure that the area which is actually being treated is the same area that the patient's doctor has marked up in the reference image. This comparison is typically a visual comparison. A technician may visually compare the two images and try to match visual landmarks between the two images. A potential problem with this visual comparison is human error in the comparison between the two images. The person making the comparison is commonly looking for very small errors, on the order of millimeters, which are normally very difficult to visually compare.

Another issue which may compound the problem is that high energy x-ray is commonly used. Accordingly, most of the x-ray goes through the body of the patient and a bony landmark is typically needed to give the person making the comparison an indication of the image reference. This visual comparison between a vague patient positioning image and a reference image may be substantially inaccurate.

Electronic portal imaging systems may produce an image without the use of film, however, a person still needs to visually compare the resulting image with a reference image. Some measuring tools may be used on the electronic portal imaging, however, the comparison is still substantially a manual process.

Although there are known algorithms for comparing two images electronically, there is typically no way of ensuring that the two images may be compared with the same frame of reference to ensure a proper match. The frame of reference of the portal imaging device is typically unknown due to mechanical errors. The gantry of the portal imaging device typically rotates around the patient. When the gantry is rotated, there is commonly a mechanical sag to the gantry which may shift the frame of reference of the image. Additionally, the detector housing of the imaging device is typically retractable into the gantry and the detector housing may not be exactly in the same position every time it is extended. Although the mechanical sag may be fairly slight, a millimeter or half a millimeter may still make a difference in patient positioning. Accordingly, the image may be offset compared to the reference image.

Once an image has been compared to the reference image, a multi-leaf collimator may be used to direct the treatment beam onto a selected area of the patient. However, without a well defined point of reference, the collimator may direct the treatment beam slightly off target.

It would be desirable to accurately identify a frame of reference so that an electronic comparison of the patient positioning image and the reference image may be performed to provide a precise and accurate comparison. It would also be desirable to accurately identify a point of reference for the multi-leaf collimator so that the collimator may be properly calibrated for the patient. The present invention addresses such needs.

For further background information on the construction and operation of a typical radiation therapy device, a brochure entitled "A Primer On Theory And Operation Of Linear Accelerators In Radiation Therapy", U.S. Department of Commerce, National Technical Information Service, December 1981, may be referenced.

SUMMARY OF THE INVENTION

The present invention relates to a system and method for finding an isocenter of an image. Once the isocenter of the image has been identified, every other point in the image may be referenced with respect to the isocenter. Accordingly, finding the isocenter may facilitate matching a frame of reference for the image with a reference image. Once a frame of reference has been identified for both images, known algorithms may be used to electronically compare the two images for an accurate and precise measurement. Additionally, finding the isocenter may also assist in calibrating a radiation therapy device, such as a collimator.

According to an embodiment of the present invention, an isocenter of an image may be found by using a multi-leaf collimator. According to this embodiment, a center leaf is projected into the center of the x-ray field with all other leaves retracted. An image is acquired. A line through the center of the center leaf is identified. This line is also a line through isocenter. The multi-leaf collimator is then rotated and a second image is acquired. A second line going through the center of the center leaf is also identified. Again this second line is also a line which goes through isocenter. Accordingly, the intersection of the two lines is isocenter.

Another method according to an embodiment of the present invention for finding isocenter uses an accessory. The accessory according to an embodiment of the present invention includes a metal marker in the center of the accessory with metal markers interspersed away from the center at a predetermined interval. An image may be acquired through the accessory, with the patient on the table. The resulting image may be analyzed to identify the position of the metal markers to determine isocenter. Once isocenter is determined, the image maybe electronically compared with a reference image.

A method according to an embodiment of the present invention for locating an isocenter of an image is presented. The method comprises projecting a center leaf of a collimator; acquiring an image through the collimator; and identifying a line traversing through the center leaf, wherein the line also traverses through an isocenter of the image.

A system according to an embodiment of the present invention for locating an isocenter of an image is also presented. The system comprises a collimator including a center leaf; and an image capturing device configured to capture an image of the collimator, wherein a line through the center leaf is identified as traversing an isocenter of the image.

In another aspect of the invention, a method according to another embodiment of the present invention for locating an isocenter of an image is also presented. The method comprises providing an accessory, wherein the accessory identifies an isocenter with a mark; acquiring an image through the accessory; and identifing an image of the mark as the isocenter.

A system according to another embodiment of the present invention for locating an isocenter of an image is also presented. The system comprises an accessory, wherein the accessory identifies an isocenter of the accessory with a mark; and an image capturing device configured to acquire an image through the accessory, wherein an image of the mark may be identified as an isocenter of the image.

DETAILED DESCRIPTION OF THE PREFERRED EMBODIMENTS

The following description is presented to enable one of ordinary skill in the art to make and to use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiments shown but is to be accorded the widest scope consistent with the principles and features described herein.

Figure 1:
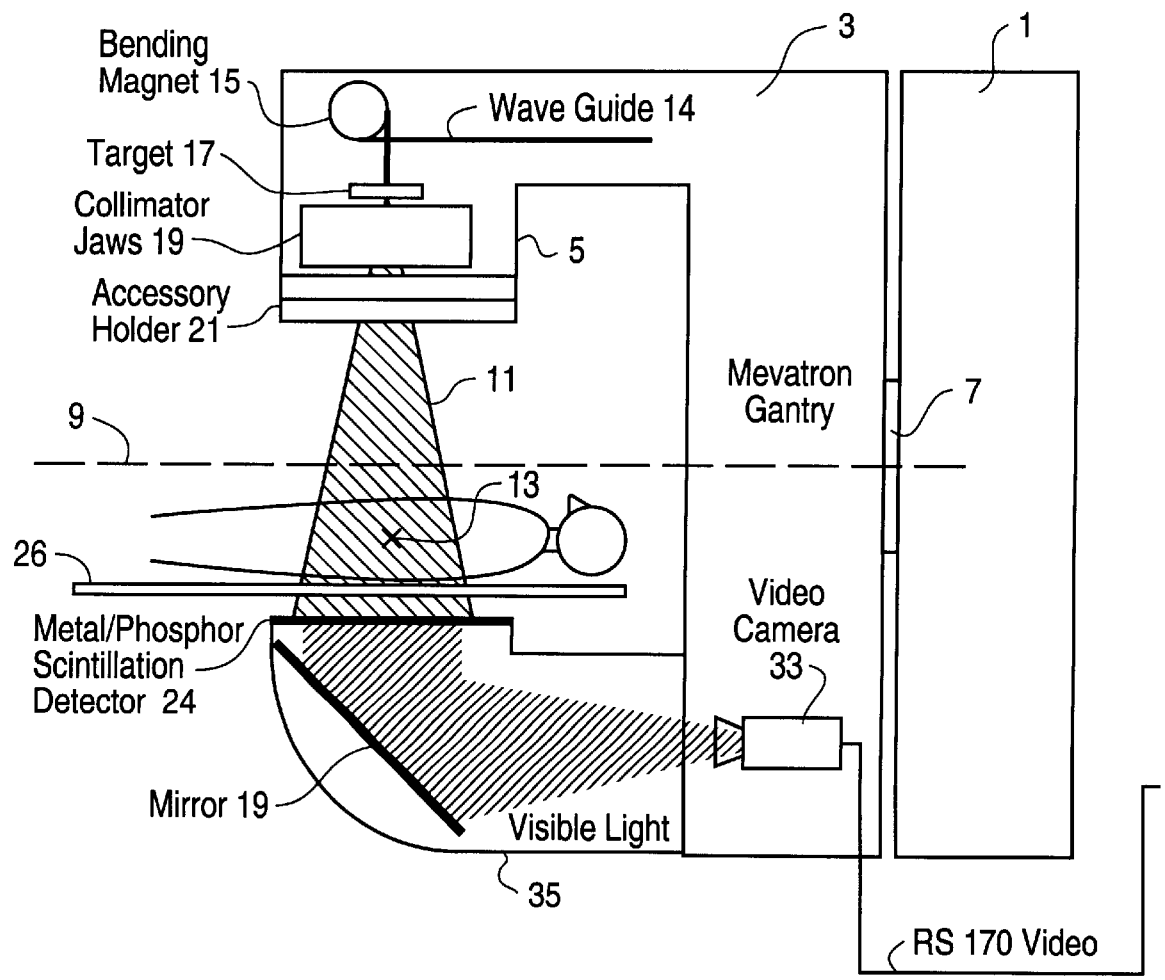
FIG. 1 illustrates a radiation beam treatment apparatus having a retractable imaging device.

One example of a linear accelerator treatment device is described in U.S. Pat. No. 5,138,647 issued Aug. 11, 1992 to Nguyen et al. FIG. 1 is a schematic diagram of a device similar to that described in U.S. Pat. No. 5,138,647. FIG. 1 shows a linear accelerator device with a stand 1 which is typically anchored firmly to the floor. Stand 1 supports a gantry 3 including a treatment head 5. Gantry 3 can be rotated on bearing 7 around a horizontal axis 9. Within gantry 3 and treatment head 5 are shown to include a waveguide 14 which channels energy. Waveguide 14 is shown to be coupled with a bending magnet 15 which directs the energy beam 11 through target 17 and into collimator 19. The resulting beam 11 may also optionally be radiated through some type of accessory in the accessory holder 21.

In stand 1, an electron injector is typically provided which supplies injector pulses to an electron gun arranged in gantry 3. Electrons are emitted from the electron gun into waveguide 14 to be accelerated. An electromagnetic field supplied to waveguide 14 typically accelerates the electrons emitted by the electron gun for forming an electron beam. In treatment head 5, the electron beam typically enters an evacuated envelop which bends the electron beam, for example, by 270 degrees. The electron beam then typically leaves the envelop through a window. If electron radiation is to be generated, a scattering foil is typically moved into the trajectory of the electron beam. If x-ray radiation is to be generated, a target is typically moved into the trajectory. The energy level of the electron beam is caused to be higher than during the generation of the electron radiation because more energy is necessary for generating x-ray radiation due to deceleration of the electrons in the target. The x-rays are typically of penetrating power and may be used for the treatment of deep seated tumors, whereas the electrons themselves may be used directly to treat more superficial cancers. During treatment, the patient rests on a treatment couch 26 and intersects the treatment area at an isocenter 13.

At a front surface of the side of gantry 3, a retractable and collapsible portal imaging detector housing 35 allows radiation treatment to be performed simultaneously with visualization of the patient's anatomy within the x-ray radiation beam. After passing through the patient's body, the x-rays impinge upon image detector 24, is reflected off mirror 19, and captured by a video camera 33. The video camera may be coupled with an integrated treatment work station wherein the functions and control of the video camera may be controlled in the same system as the functions and control of gantry 3 adjustments. Alternatively, video camera 33 may be coupled with a computer system which may be electronically accessible by another computer system, wherein the second computer system controls the motions and adjustments of gantry 3. Yet another alternative is for video camera 33 to be coupled to a video camera computer system while the motions and control of gantry 3 are coupled to a separate computer system.

Figure 2:
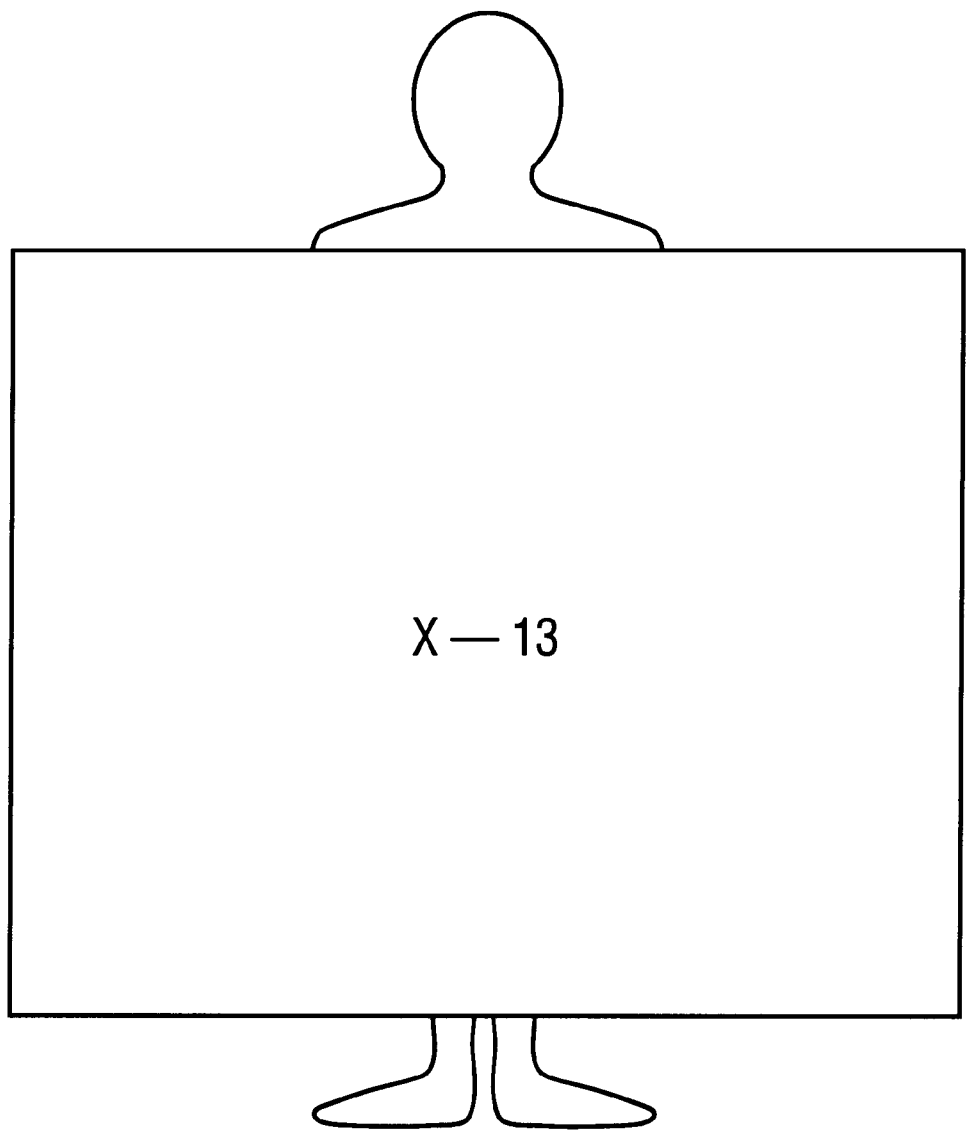
FIG. 2 is an illustration of isocenter.

FIG. 2 is an illustration of isocenter. FIG. 2 illustrates a patient with isocenter 13 located at the three-dimensional center of the treatment field. Isocenter 13 is located in the center of the treatment field from a perspective above the patient, as well as the center of the patient within the treatment field as seen from a perspective beside the patient (see isocenter 13 of FIG. 1). All other points within the treatment field may be defined relative to isocenter 13. For example, patient positioning, treatment field size, and treatment field shape may be defined relative to isocenter 13. A two-dimensional image also has a two-dimensional isocenter corresponding to the three-dimensional isocenter. Once the two-dimensional isocenter is determined, then all equipment calibrations, image comparisons and patient positioning may be performed with respect to the isocenter. If detector housing 35 is centered and gantry 3 is centered above detector housing 35, then isocenter should be at the center of the image. However, if detector housing 35 is not exactly centered or if gantry 3 is not centered above detector housing 35, then it is typically unclear where isocenter is located.

Figure 3:
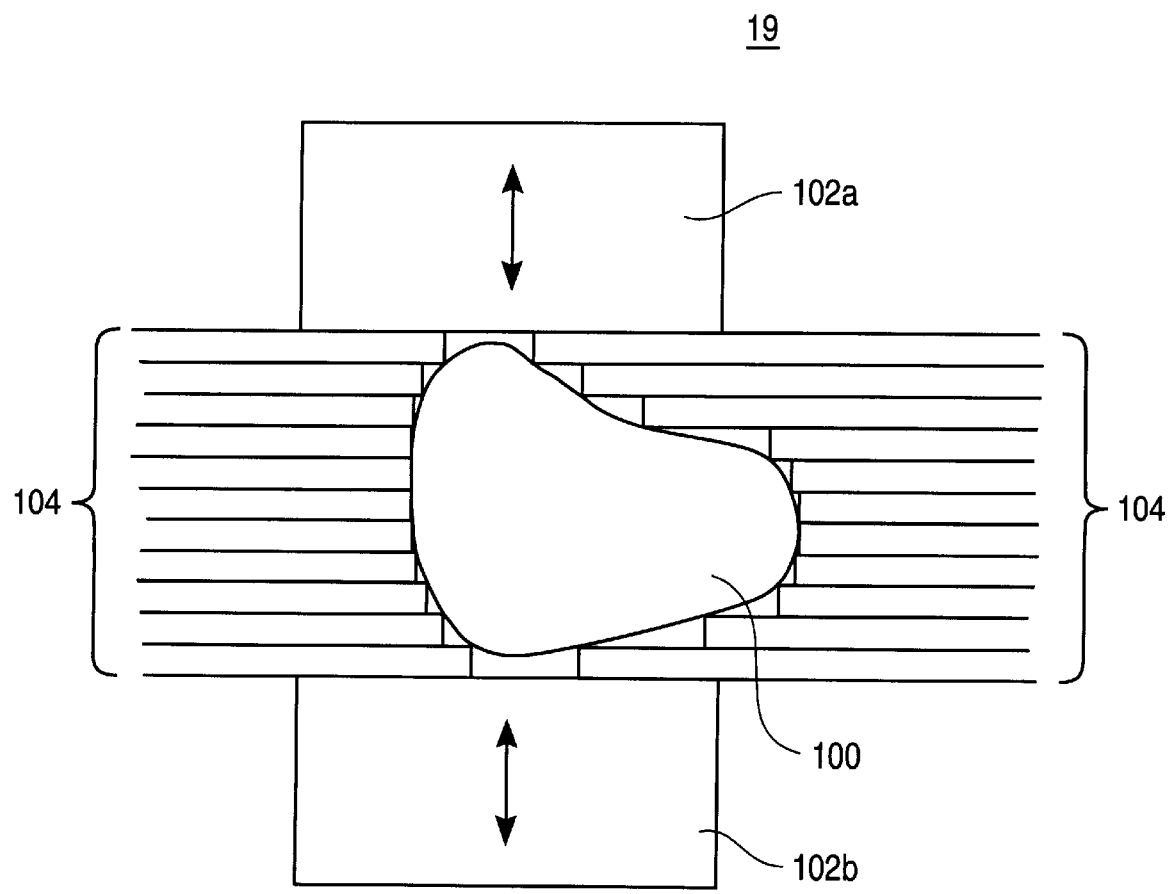
FIG. 3 is an illustration of a multi-leaf collimator.

FIG. 3 is an illustration of a multi-leaf collimator 19. In the example shown in FIG. 3, a multi-leaf collimator 19 is shown to be shaped around a target 100, such as a tumor. Tumor shapes are often irregular, and a multi-leaf collimator, such as the multi-leaf collimator manufactured by Siemens, facilitates minimal radiation being applied to non-tumor tissues by shaping itself close to the shape of the tumor.

Multi-leaf collimator 19 is shown to include leaves 104 located on either side of target 100. Additionally, multi-leaf collimator 19 may also include a set of jaws 102*a*–102*b* located perpendicular to leaves 104. Jaws 102*a*–102*b* may be movable in a direction perpendicular to the longitudinal axis of leaves 104. Accordingly, jaws 102*a*–102*b* may approach each other to reduce the size of the x-ray field, or move away from each other to increase the size of the x-ray field. Likewise, each leaf 104 may be moved along it's longitudinal axis toward or away from an opposing leaf 104 to customize the x-ray field for a particular target 100, such as a tumor. The x-ray field is allowed to pass within the space between leaves 104 and jaws 102*a*–102*b*.

When the multi-leaf collimator 19 is shaped substantially similar to target 100, it facilitates a very high dosage to be applied to target 100, while still protecting healthy tissue and vital organs. However, even if multi-leaf collimator 19 is shaped substantially similar to target 100, healthy tissue and vital organs may be damaged if multi-leaf collimator 19 is not matched to the location of target 100.

Figure 4:
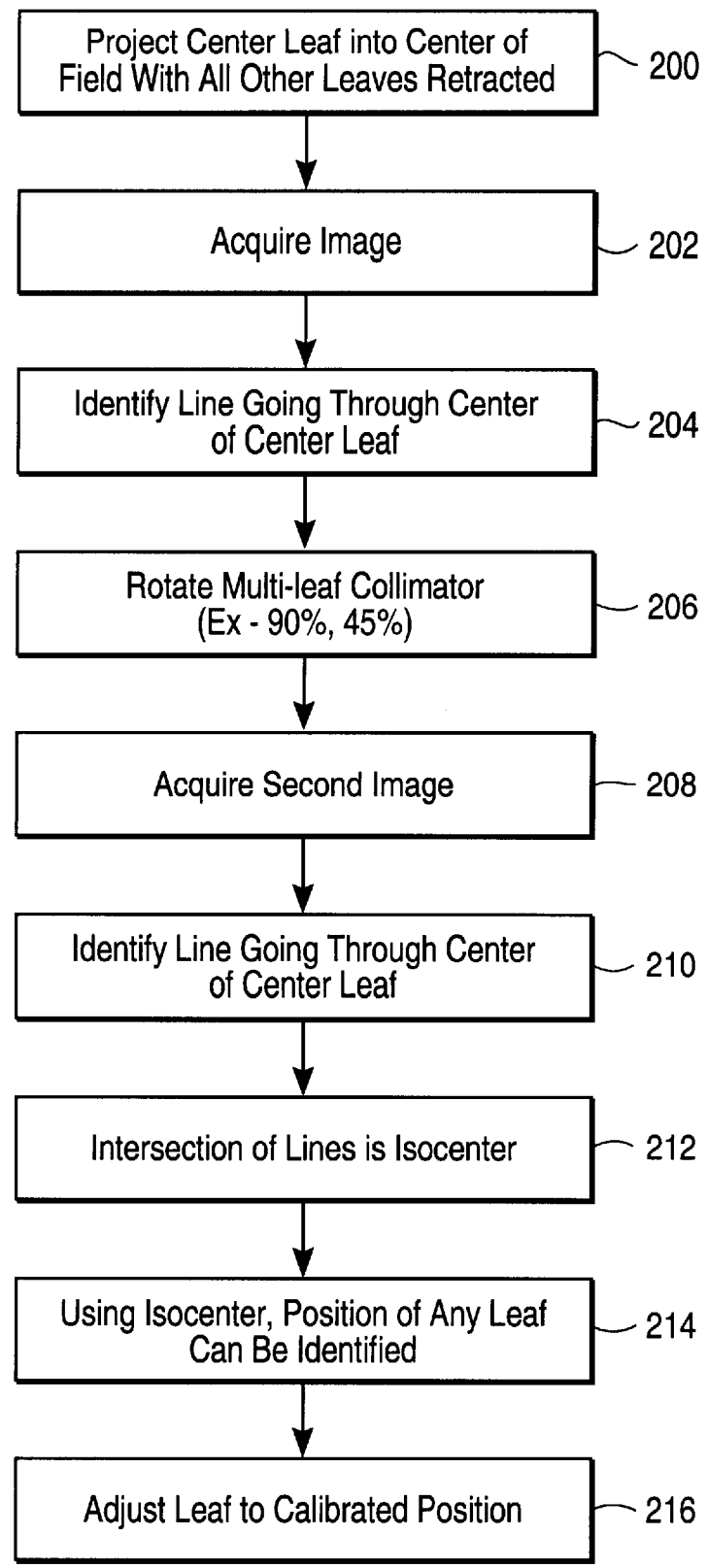
FIG. 4 is a flow diagram according to an embodiment of the present invention for locating isocenter by using a multi-leaf collimator.
Figure 5A:
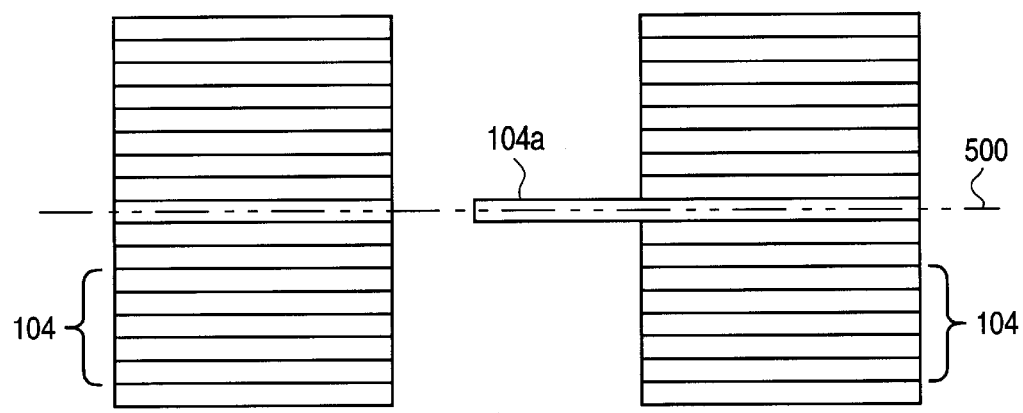
FIGS. 5a–5c depict a multi-leaf collimator in various stages of determining isocenter according to an embodiment of the present invention.
Figure 5B:
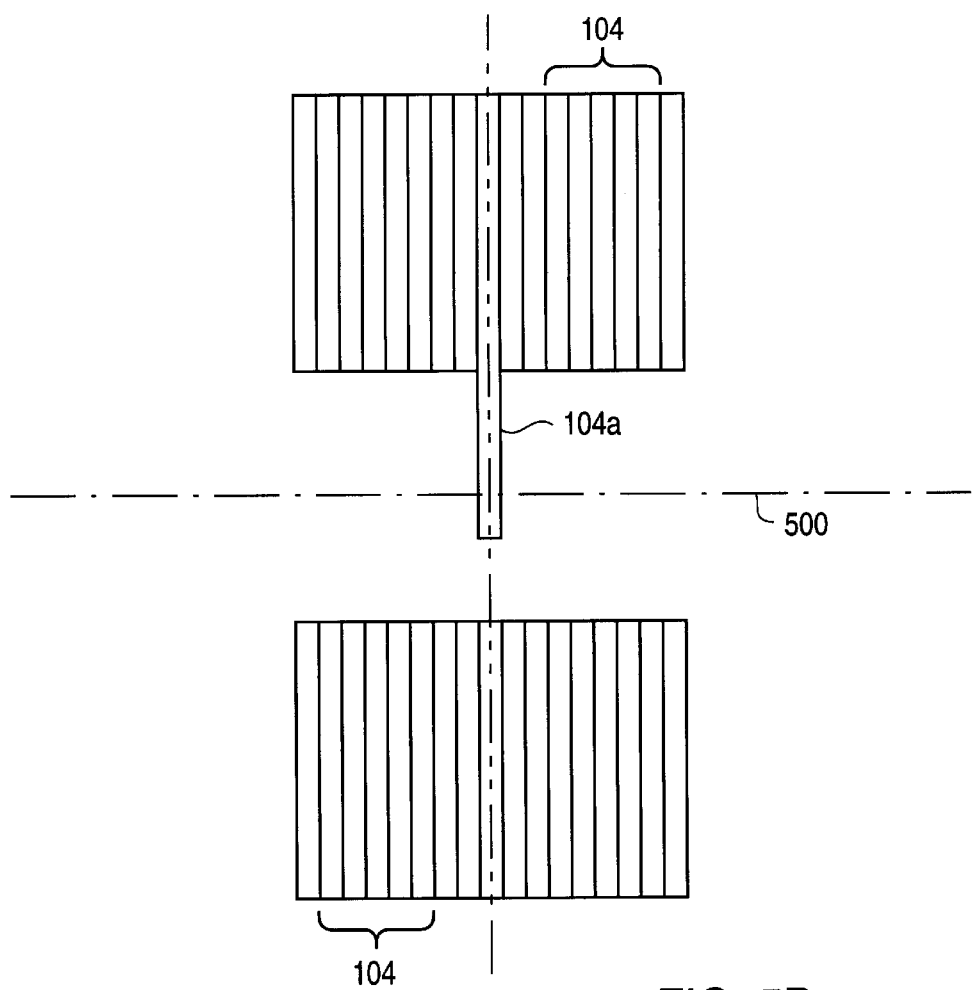
Figure 5C:
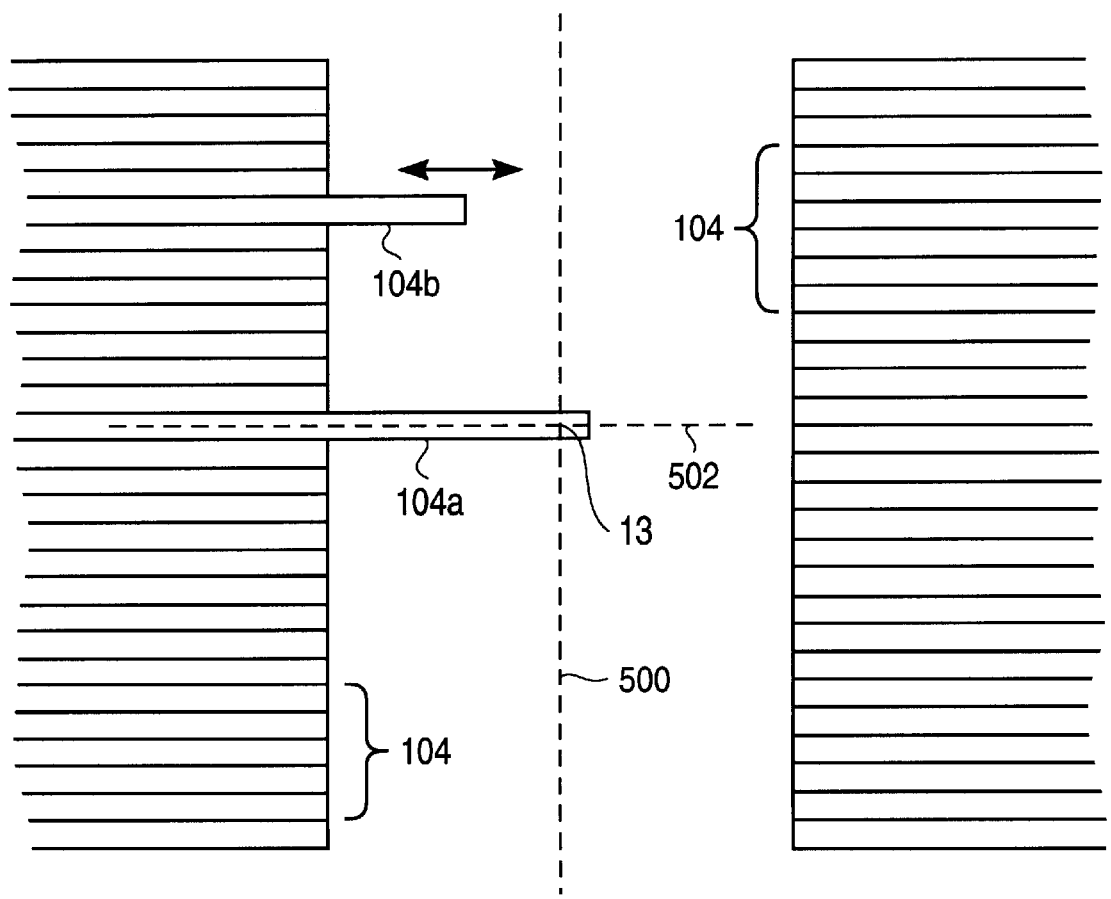

FIG. 4 is a flow diagram of a method according to an embodiment of the present invention for locating isocenter by utilizing a multi-leaf collimator. The method shown in FIG. 4 may be referenced in conjunction with FIGS. 5*a*–5*c*. FIGS. 5*a*–5*c* illustrate a multi-leaf collimator in various positions at various steps described in the method according to an embodiment of the present invention exemplified in FIG. 4.

A center leaf of a multi-leaf collimator is projected into the center of a field with all other leaves retracted (step 200). In FIG. 5*a*, a center leaf 104*a* is shown to be projected into the center of a field, such as an x-ray field, with all other leaves 104 retracted. In the example of a Siemens multi-leaf collimator, there may be 29 leaves on each side of the field for a total of 58 leaves plus two jaws (shown in FIG. 3). In this example, a center leaf is leaf 15 (the 15$^{th}$ leaf counted from either direction).

An image is acquired through the multi-leaf collimator (step 202). A line through the longitudinal center of the center leaf is then identified (step 204). In the example shown in FIG. 5*a*, the line through the longitudinal center of center leaf 104*a* is line 500. Since isocenter is theoretically in the center of the field, and the shape of the field is defined by the multi-leaf collimator, the center leaf 104*a* should be located in the middle of the field. Additionally, the width of each leaf is expected to be uniform and all of the leaves are positioned flush against each other so that the width of the collimator perpendicular to the longitudinal axis of the leaves are expected to remain constant. Accordingly, line 500 is a line moving through isocenter.

Once line 500 has been identified, the multi-leaf collimator is then rotated (step 206). For example, the multi-leaf collimator may be rotated 90 degrees or 45 degrees. In the example shown in FIG. 5*b*, the multi-leaf collimator has been rotated 90 degrees as compared to its position shown in FIG. 5*a*.

A second image is then acquired by allowing the field to flow through the collimator (step 208). Once the second image has been acquired, a second line moving through the longitudinal center of center leaf 104*a* is identified (step 210). In the example shown in FIG. 5*b*, the second line moving through the longitudinal center of center leaf 104*a* is shown to be line 502.

The intersection of lines 500 and 502 i;s then identified as isocenter (step 212). If the multi-leaf collimator is rotated at a different angle, such as two 45 degree turns, and a third line (not shown) is identified, then the intersection of all three lines would be identified as isocenter. If fewer than all lines intersect at one point, then the point at which the majority of the lines intersect would be identified as isocenter and the remaining lines may be attributed to mechanical error.

Once isocenter is located, the position of any leaf may be identified with respect to isocenter 13 (step 214). Accordingly, the position of any leaf in the multi-leaf collimator may be calibrated with respect to isocenter 13 (step 216). In the example shown in FIG. 5*c*, a second leaf 104*b* is shown to be in a specified position. The position of leaf 104*b* may be calibrated with respect to isocenter 13 to ensure accuracy and precision despite mechanical errors in the positioning of leaf 104*b*.

Figure 6:
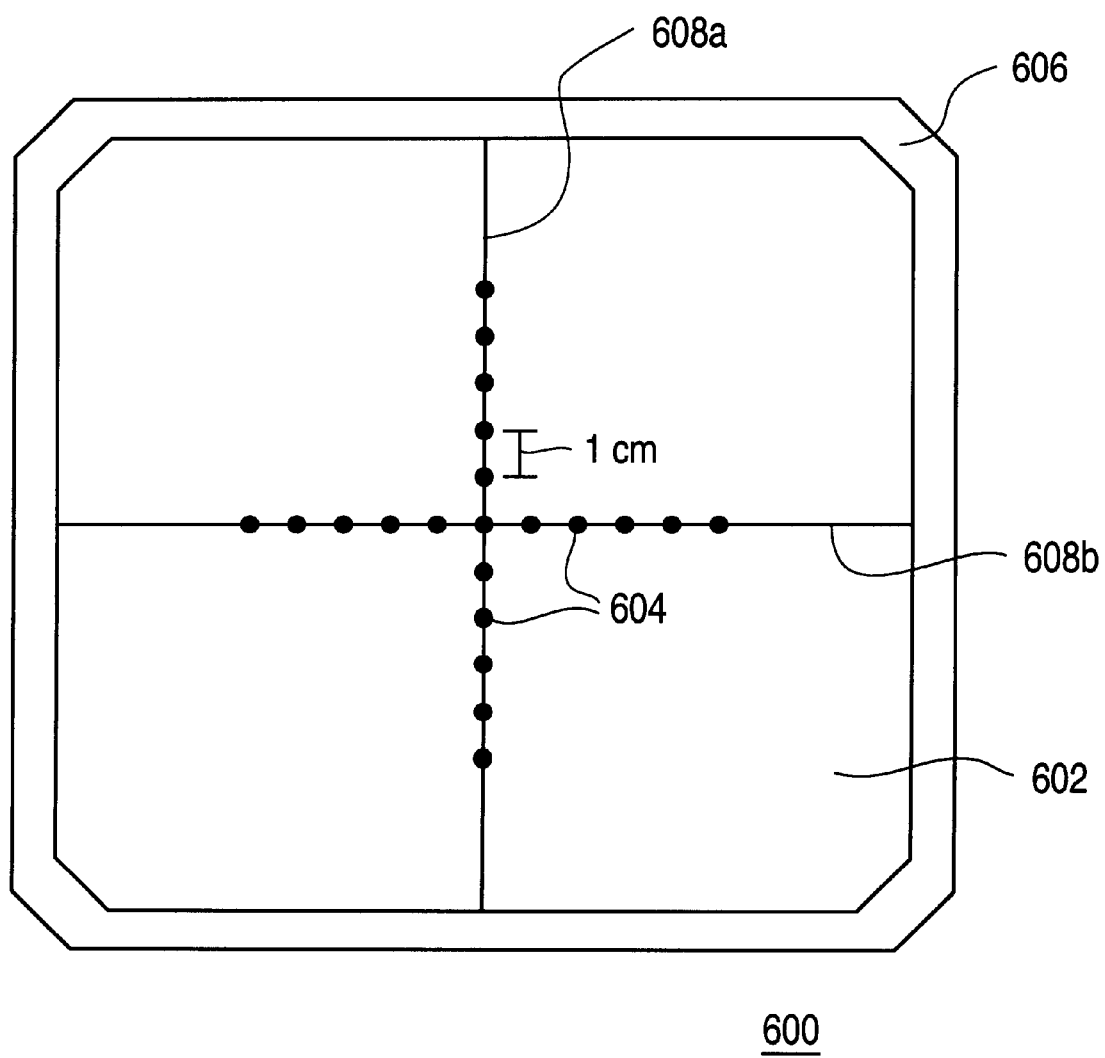
FIG. 6 is an illustration of an accessory according to an embodiment of the present invention which may be used to determine isocenter.

FIG. 6 is an illustration of an accessory which may be used to find isocenter according to another embodiment of the present invention. Accessory 600 may be a clear piece of plastic 602 surrounded by a frame 606. The frame 606 should be a compatible size with the accessory holder of the radiation treatment apparatus, such as accessory holder 21 of the radiation treatment apparatus of FIG. 1. Examples of the size of accessory 600 include approximately 21 cm×25 cm, or 25 cm×25 cm. Within clear plastic 602, metal markers 604 may be placed. A metal marker should be located in the center of the clear plastic 602, preferably with several other metal markers spaced apart at a predetermined distance such as approximately 5 mm. The metal marker may be a spot of metal embedded or located in the plastic 602. The metal marker is preferably a metal which will stop radiation, such as Tungsten, and large enough to show in an image. An example of a size of a metal marker is approximately 1–2 mm in diameter. Metal markers 604 may be spaced apart on an X and Y axis 608*a*–608*b*. A metal marker should be placed at the intersection of the X and Y axis 608*a*–608*b* to indicate isocenter. The center metal marker placed at the X and Y axis 608*a*–608*b* may be a larger marker than some of the other markers. For example, the center metal marker may be 2 mm in diameter, followed by a predetermined number of smaller metal markers, such as four metal markers 1 mm each in diameter, then followed by another 2 mm metal marker, followed again by four more 1 mm metal markers.

The x-ray field is typically at such a high energy that most of the x-ray beam will move through the body of the patient. Accordingly, only hard locations in the patient's body, such as a bone structure, may be viewed in an image taken of the patient. However, if the high energy x-ray field is shot through accessory 600 as well as the patient, then a resulting image should show metal markers 604. The center metal marker is expected to be isocenter of the image. If the center metal marker is not visible in the image (for example a bone structure is also located at isocenter) then the remaining metal markers 604 may be used to determine isocenter since all the metal markers are evenly spaced at a predetermined distance, such as 5 mm.

Figure 7:
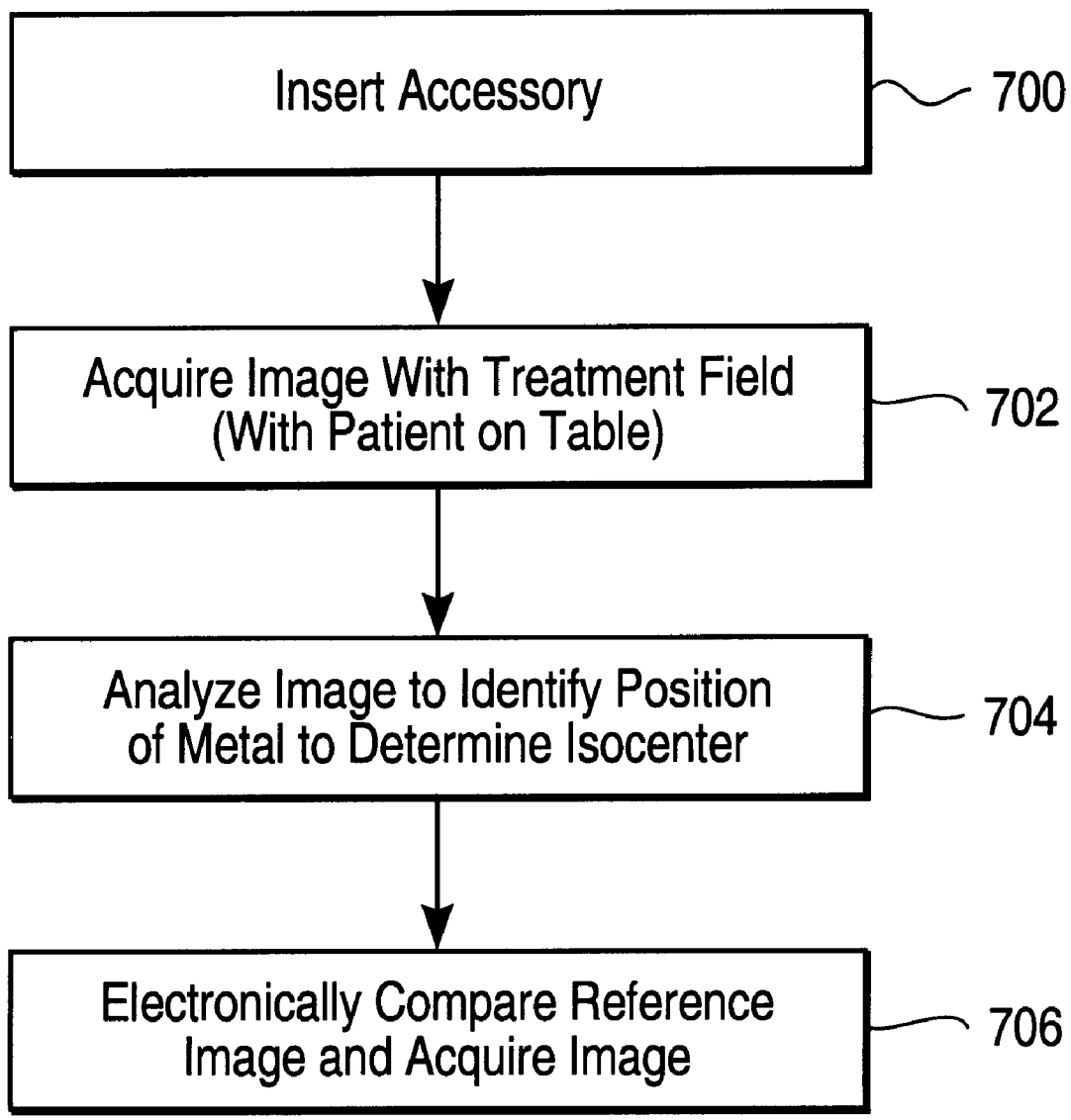
FIG. 7 is a flow diagram of a method according to an embodiment of the present invention for finding isocenter by using an accessory.

FIG. 7 is a flow diagram of a method according to an embodiment of the present invention for locating isocenter by using an accessory. Accessory 600 is inserted into a radiation treatment apparatus, such as into accessory holder 21 of the apparatus shown in FIG. 1 (step 700). An image is then acquired with the treatment field moving through accessory 600 as well as the patient positioned on the table (step 702). The image is then analyzed to identify the position of metal markers 604 to determine isocenter of the image (step 704). Once isocenter has been identified, the acquired image may be electronically compared to a reference image (step 706). The electronic comparison may be performed through known algorithms, such as the Basic Pattern Recognition Module included in Matrox Imaging Library (MIL) manufactured by Matrox.

Although the present invention has been described in accordance with the embodiment shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for locating an isocenter of an image comprising:
   projecting a center leaf of a collimator;
   acquiring an image through the collimator; and
   identifing a line traversing through the center leaf, wherein the line also traverses through an isocenter of the image.

2. The method of claim 1, wherein the line traverses through the center leaf along a longitudinal axis along a center of the center leaf.

3. The method of claim 1, further comprising rotating the collimator.

4. The method of claim 3, further comprising acquiring a second image through the collimator.

5. The method of claim 3, further comprising acquiring a second image through the collimator.

6. A system for locating an isocenter of an image comprising:
   means for projecting a center leaf of a collimator;
   means for acquiring an image through the collimator; and
   means for identifying a line traversing through the center leaf, wherein the line also traverses through an isocenter of the image.

7. The system of claim 6, wherein the line traverses through the center leaf along a longitudinal axis along a center of the center leaf.

8. The system of claim 6, further comprising means for rotating the collimator.

9. The system of claim 6, further comprising means for acquiring a second image through the collimator.

10. The system of claim 6, further comprising means for identifying a second line traversing through the center leaf, wherein the second line also traverses through the isocenter of the image.

11. A system for locating an isocenter of an image comprising:
    a collimator including a center leaf; and
    an image capturing device configured to capture an image of the collimator, wherein a line through the center leaf is identified as traversing an isocenter of the image.

12. The system of claim 11, wherein the image capturing device is also configured to capture a second image of the collimator, wherein a second line through the center leaf is also identified as traversing through the isocenter of the second image.

13. The system of claim 12, wherein the second image is an image of the collimator rotated relative to the collimator in the first image.

14. A method for locating an isocenter of a body during a radiation therapy treatment, comprising:
    providing an accessory between a radiation source and the body, wherein the accessory identifies an isocenter with a mark;
    directing a radiation beam through the accessory and the body;
    acquiring an image of the mark and the body; and
    identifying an image of the mark as the isocenter.

15. The method of claim 14, wherein the mark is of a material that substantially stops radiation.

16. The method of claim 14, further comprising a second mark included in the accessory, wherein the second mark is located at a known distance from the mark identifying the isocenter.

17. The method of claim 14, wherein the accessory includes a clear portion.

18. A system for locating an isocenter of a body during a radiation therapy treatment, comprising:
    means for providing an accessory between a radiation source and the body, wherein the accessory identifies an isocenter with a mark;
    means for directing a radiation beam through the accessory and the body;
    means for acquiring an image of the mark and the body; and
    means for identifying an image of the mark as the isocenter.

19. The system of claim 18, wherein the mark is of a material that substantially stops radiation.

20. A system for locating an isocenter of a body during a radiation therapy treatment, comprising:
    an accessory positioned between a radiation source and the body, wherein the accessory identifies an isocenter of the accessory with a mark;
    said radiation source directing a radiation beam through the accessory and the body; and
    an image capturing device configured to acquire an image of the mark and the body, wherein an image of the mark may be identified as an isocenter of the image.

21. The system of claim 20, wherein the accessory further includes a clear portion.

22. The system of claim 20, wherein the mark is of a material that substantially stops radiation.

23. The system of claim 20, wherein the mark includes tungsten.

24. The system of claim 20, further comprising a second mark included in the accessory, wherein the second mark is located at a known distance from the mark identifying the isocenter.

25. The system of claim 20, further comprising a plurality of marks included in the accessory, wherein each of the plurality of marks is located at a known distance from another of the plurality of marks.

* * * * *